(12) United States Patent
Gordon et al.

(10) Patent No.: US 12,220,121 B2
(45) Date of Patent: Feb. 11, 2025

(54) SUTURE TRANSFER DEVICE

(71) Applicants: Leonard Gordon, San Francisco, CA (US); Joshua Gordon, San Francisco, CA (US)

(72) Inventors: Leonard Gordon, San Francisco, CA (US); Joshua Gordon, San Francisco, CA (US)

( * ) Notice: Subject to any disclaimer, the term of this patent is extended or adjusted under 35 U.S.C. 154(b) by 924 days.

(21) Appl. No.: 16/454,017

(22) Filed: Jun. 26, 2019

(65) Prior Publication Data

US 2019/0388086 A1  Dec. 26, 2019

Related U.S. Application Data

(60) Provisional application No. 62/763,646, filed on Jun. 26, 2018.

(51) Int. Cl.
*A61B 17/04* (2006.01)
*A61B 17/17* (2006.01)

(52) U.S. Cl.
CPC ...... *A61B 17/0482* (2013.01); *A61B 17/0469* (2013.01); *A61B 17/0467* (2013.01); *A61B 17/1796* (2013.01)

(58) Field of Classification Search
CPC ............ A61B 17/1796; A61B 17/0469; A61B 17/0482; A61B 17/320016; A61B 17/32002; A61B 2017/320024; A61B 2017/32004; A61B 2017/320052
See application file for complete search history.

(56) References Cited

U.S. PATENT DOCUMENTS

| | | | |
|---|---|---|---|
| 5,151,559 A | 9/1992 | Conru et al. | |
| 5,269,290 A * | 12/1993 | Barrett | A61B 17/320016 600/101 |
| 5,342,369 A | 8/1994 | Harryman | |
| 5,520,693 A * | 5/1996 | McGuire | B25G 3/26 606/88 |
| 5,690,677 A | 11/1997 | Schmieding | |
| 5,827,312 A * | 10/1998 | Brown | A61B 17/320016 604/164.11 |
| RE36,020 E | 12/1998 | Moore | |
| 5,948,002 A * | 9/1999 | Bonutti | A61B 17/3468 606/232 |
| 6,245,011 B1 * | 6/2001 | Dudda | A61B 17/320016 600/106 |
| 6,245,081 B1 | 6/2001 | Bowman | |
| 8,282,643 B2 * | 10/2012 | Dross | A61B 17/1684 606/86 R |

(Continued)

*Primary Examiner* — Matthew J Lawson (57) ABSTRACT

A suture transfer device and method of use provides the suture transfer device to facilitate passage of suture through a channel bored through a bone. The suture transfer device may also be installed upon a surgical drill. The device extends through bone tissue providing a temporarily installed suture passage with an overall cylindrical configuration and a linear trough, the device can be included on a bone drill during the drilling process, with the device deployed within the drilled channel within the bone upon completion of the drilled channel in the bone, providing smooth passage of one or more sutures during tissue repair through the linear trough, the device further removed upon completion of the surgery without disruption of the suture or sutures. Kits are also provided.

6 Claims, 7 Drawing Sheets

(56) References Cited

U.S. PATENT DOCUMENTS

| | | | |
|---|---|---|---|
| 8,585,714 B2* | 11/2013 | Weisel | A61B 17/0469 |
| | | | 606/139 |
| 8,801,727 B2 | 8/2014 | Chan | |
| 8,808,329 B2 | 8/2014 | Bonutri | |
| 9,138,223 B2 | 9/2015 | Jolly | |
| 11,266,492 B2* | 3/2022 | Hoopes | A61B 17/1778 |
| 11,382,637 B1* | 7/2022 | Schub | A61B 17/1617 |
| 2007/0088362 A1* | 4/2007 | Bonutti | A61B 17/82 |
| | | | 606/99 |
| 2018/0042631 A1* | 2/2018 | Garlock | A61B 17/3211 |
| 2019/0125367 A1* | 5/2019 | Acevedo | A61B 17/1682 |

* cited by examiner

SUTURE TRANSFER DEVICE

CROSS REFERENCE TO RELATED APPLICATIONS

This application claims the benefits of U.S. Provisional Application 62/763,646 filed Jun. 26, 2018.

I. BACKGROUND OF INVENTION

1. Field of the Invention

A suture transfer device installed upon a surgical drill for drilling through bone tissue providing a temporarily installed suture passing device being overall cylindrical with a linear trough and an end expansion. The device is included on a bone drill and is deployed within the drilled channel within the bone, providing a passage within the trough for the passage of one or more sutures during tissue repair. Once the tissue repair is completed, the device may be removed without disruption of the suture or sutures. A method for the installation and removal is also disclosed.

2. Description of Prior Art

A preliminary review of prior art patents was conducted by the applicant which reveal prior art patents in a similar field or having similar use. However, the prior art inventions do not disclose the same or similar elements as the present suture transfer device, nor do they present the material components in a manner contemplated or anticipated in the prior art.

| Patent No. | Issue Date | Inventor |  |
|---|---|---|---|
| 9138223 | 09/22/2015 | Jolly | Drill pin for suture passing |
| 8808329 | 08/19/2014 | Bonutri | Bone anchors |
| 8801727 | 08/12/2014 | Chan | Suture passer |
| 6245081 | 06/12/2001 | Bowman | Suture buttress |
| RE 36020 | 12/29/1998 | Moore | Parallel hole guide |
| 5951559 | 09/14/1999 | Burkhart | Method for installing suture anchor |
| 5690677 | 11/25/1997 | Schmieding | Method for installing suture anchor |
| 5342369 | 08/30/1994 | Harryman | Drill through suture guide |

The most similar patents dealt with a suture guide through which a drill is passed—Jolly and Harryman. The rest are simply items involving a tubular structure within the device for drilling or the passage of a suture. However, none of them involve the structure, utility or method disclosed in the present suture transfer device.

II. SUMMARY OF THE INVENTION

In the field of surgery cables or suture must often be passed through a bone or other solid structure. Many methods are employed to do so including cannulated needles or tubes or lassos to capture and drag the cable/suture through. These may be solid or flexible. Passage of these passage aids can be difficult and often allows only one passage of the cable/suture as the device (such as a cannulated needle) cannot be removed after multiple passes.

The current invention consists of a device that can be drilled into the bone, partly removed but retaining a part round structure for the passage of the cable/suture. Finally, the device is removed and the cable/suture is retained in position. In the case of metal cables, which may be monofilament or multifilament, one cable may be attached to another cable by use of a crimp. Any cable or suture may be used.

III. BRIEF DESCRIPTION OF THE DRAWINGS

The following drawings provide descriptions of some embodiments of the invention.

IV. DESCRIPTION OF THE PREFERRED EMBODIMENTS

A suture transfer device is used for installation into a bone to allow for and accommodate passage of a connection element, such as suture, cable, etc., through a channel or bore through a bone until conclusion of a surgical procedure, after which time the suture transfer device is removed, leaving the passed connection device within the bone without interfering with the installed surgical sutures or cables, etc.

In surgery involving the passage of suture, cable, or other connection elements through a bore or channel created in a bone, a common difficulty occurs in obtaining clear access to the openings of the bore due to the soft tissue, bony obstruction or issues with trajectory or maintenance of a clear path. After drilling a bore, the soft tissue, bony obstruction or issues with trajectory or maintenance of a clear path can obscure the openings and make it difficult to insert and pass sutures or cables through the channel bored through the bone. The device of the present invention addresses this problem, provides better access to pass a connection element through a channel bored through a bone and allows a connection element to be passed multiple times through the device and the device to be removed without interfering with the connection element. The open trough section of the semi-cylindrical portion of the device provides these advantages which cannot be achieved with a solid tube.

In a preferred embodiment, the suture transfer device provides for passage of one or more connection elements, such as sutures or surgical cables, stability of the connection elements during installation and fixation through the conclusion of the surgical procedure and final removal of the device from the bone without interruption of the sutures, cable or tissues involved in the surgical procedure. The suture transfer device comprises a semi-cylindrical portion with an inner surface and an outer concave surface. The outer convex surface is sized to approximate the size of a channel bored into a bone. The semi-cylindrical shape is most preferred because the vast majority of channels bored through bones by rotating bits are circular in shape.

Figure 3:
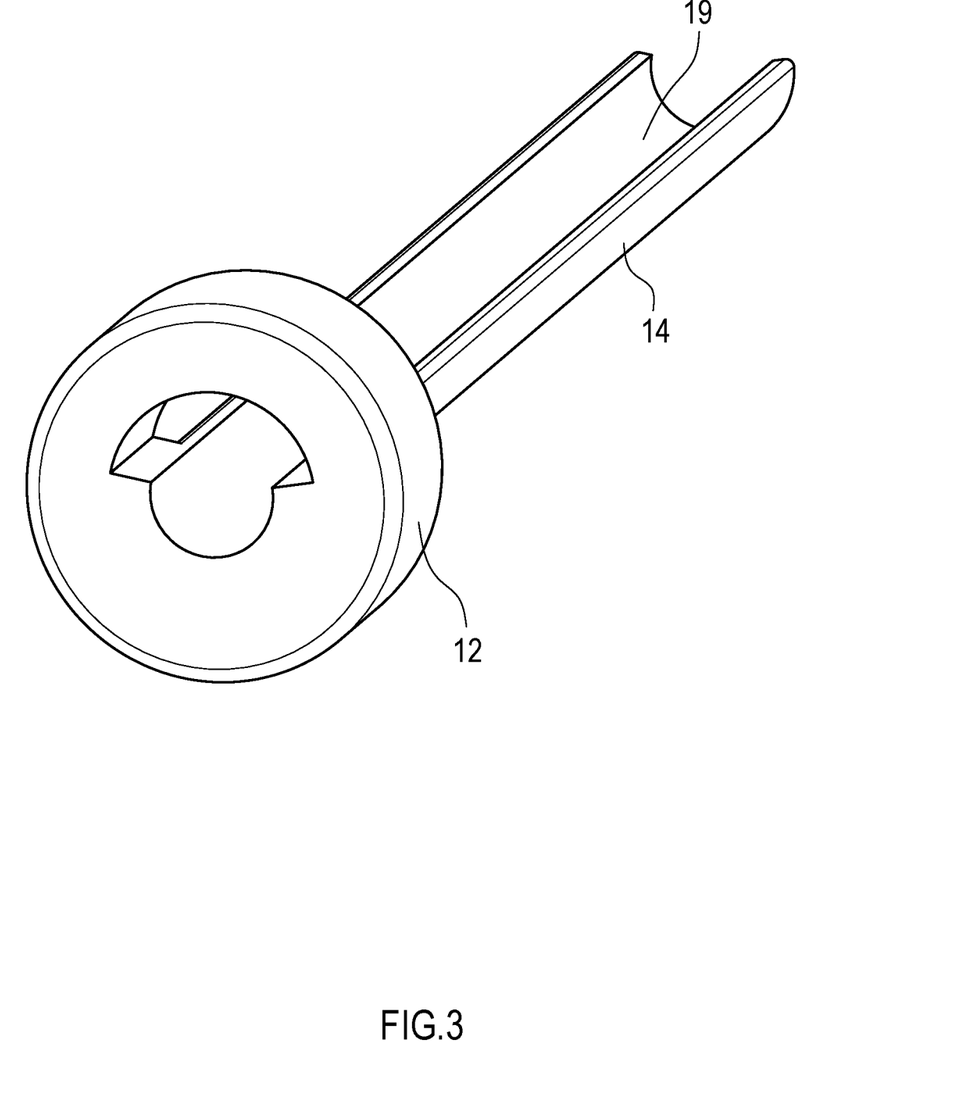
FIG. 3 is an end view of the suture transfer device.
Figure 4:
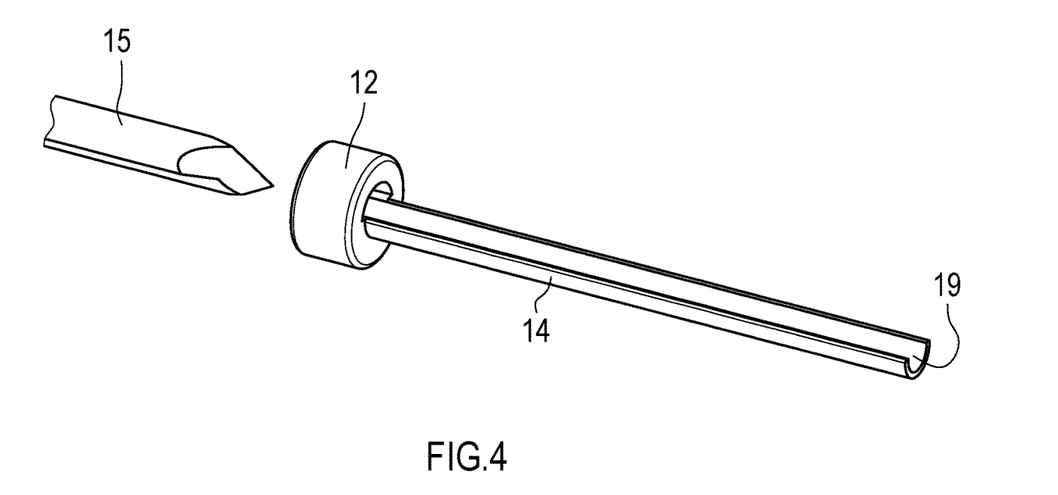
FIG. 4 is a perspective view of the suture transfer device upon withdrawal of the drill bit.
Figure 5:
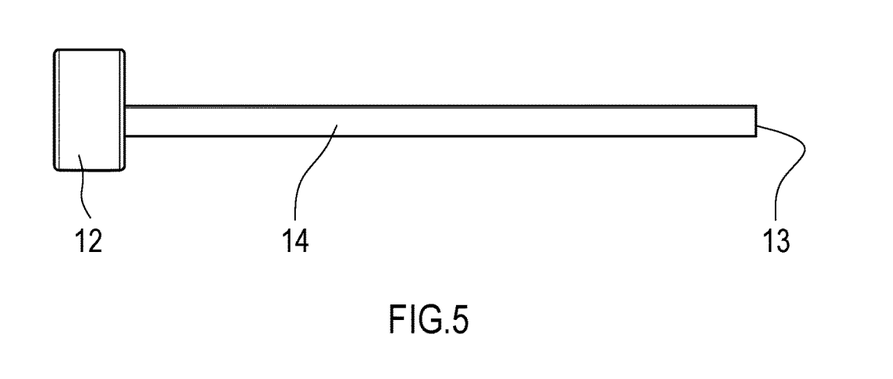
FIG. 5 is a side scale view of the suture transfer device in a specific embodiment suited for installation within a 0.62", hole in a bone.

In preferred embodiments, the suture transfer device also comprises an extension attached to an end of the semi-cylindrical portion. The extension serves to improve the convenience of the insertion of the device into the bored channel through a bone, positioning the opening of the semi-cylindrical portion of the device to provide optimal access for suture or cable, as well as removal of the device from the channel. The extension can be selected from a variety of forms and positioned in a variety of way. For example, an extension can be an extension from one end of the device that protrudes linearly along the central longitudinal axis of the semi-cylindrical portion. In another example, the extension can be a collar shape as shown in FIG. 3. In another example, the extension can protrude at an angle from the central longitudinal axis of the semi-cylindrical portion, said angle being preferred to be between 1 degree and 90 degrees.

In preferred embodiments, the semi-cylindrical portion can comprise an outer surface defining a circumference representing preferably at least 5% of a cylinder and preferably up to 90% of a cylinder which can be adjusted to accommodate instruments, implants or visualization methods. More preferred are devices comprise an outer surface defining a circumference representing a range of 20% to 80% or in the range of 30% to 90%. Other preferred embodiments comprise an outer surface defining a circumference representing 40% to 60%. One of skill in the art will recognize that the design of any particular semi-cylindrical portion of the device will account for factors that include the circumferential size of the channel drilled through the bone, the size of the suture or cable, etc., that will pass through the device and determine the size of outer surface of the semi-cylindrical portion best suited to the surgical application between 5% and 90% of the circumference of a full cylinder. For example, for larger diameter, stiff connection elements, a suture transfer device with an outer surface defining a smaller percentage of the circumference of a cylinder can be adequate. Preferably, one can take 50% of the circumference of a cylinder as a starting point and increase of decrease that amount as preferred for any particular application. Straightforward tests may be conducted to determine the optimal parameters.

In preferred embodiments, the length is also chosen to be sized appropriately for the length of the channel to be bored through a bone. It is preferred that the semi-cylindrical portion be sized to exceed the length of the channel and protrude out of each end of the channel. However, the length should not be so long that the length would not fit in the surgical site or cause difficulty in positioning the device in the channel. The outer surface of the device should have a circumference that is appropriate for the size of the channel bored through a bone so that it can be inserted and withdrawn without difficulty. In preferred embodiments it is appropriate that the device have a circumference that is smaller than the diameter of the channel to facilitate insertion and removal. In preferred embodiments the device can be sized to be 5%, 10%, 15%, 20%, 30%, 40% or 50% smaller than the circumference of the channel. Other sizes can be chosen by the operating surgeon as is appropriate and facile in his view. The only limitation is that the device is large enough to provide a reliable path for the connection element as it passed through the channel with the device in place. If the device is too small compared to the size of the channel, the connection element could possibly loose the guidance provided by the device as it passes through the channel. If the device is too large, it may be difficult to install in the channel.

In preferred embodiments the semi-cylindrical portion of the suture transfer device has an inner concave surface. In other embodiments, the inner surface can have other shapes. In some preferred embodiments the semi-cylindrical portion can have a non-concave inner surface such as a multi-angular inner surface. A multi angular inner surface can comprise a number of flat surfaces running the length of the central longitudinal axis of the semi-cylindrical portion. The number of surfaces can be two in which case the semi-cylindrical portion would have a V-shaped interior surface running parallel to the central longitudinal axis of the portion. The number of surfaces can be three, four, five, six, seven or more.

In additional preferred embodiment, the inner surface of the semi-cylindrical portion of the suture transfer device is adapted to accommodate a drill bit. The shape of the inner surface is designed to match the outer surface of a drill bit. For example, a concave inner surface can be matched with a drill bit that has a convex outer surface. That type of suture transfer device and drill bit pairing is illustrated in the Figures. However, in other examples, the inner surface may have a multi-angular surface as described above and be matched to a drill bit that has a reciprocal multi-angular external surface. Other configurations can also be provided such as combining elements of concave and flat surfaces running the length of the longitudinal axis of the device. The design of the inner surface of the semi-cylindrical portion is thereby not limited by the drawings and can be provided in a variety of shapes.

In another preferred embodiment, the suture transfer device provides for inclusion of a surgical drill bit through the suture transfer device, removal of the drill bit, passage of one or more sutures or surgical cables, stability of the sutures or cable during installation and fixation through the conclusion of the surgical procedure and final removal from the bone without interruption of the sutures, cable or tissues involved in the surgical procedure.

A first embodiment of the suture transfer device is shown in FIGS. 1-5. Referring to FIG. 1A, in this embodiment, the suture transfer device 14 defines a semi-cylindrical portion, sometimes referred to as a boat or trough member or portion, extending from a collar 12 having a central bore with an extended arch portion integrated onto a first end of the boat member, with a second end of the boat member defining an insertion end 13. The contour of the boat member is a half cylinder (FIG. 3), defining an inner concave portion and an outer convex portion. The inner concave portion 19 (FIG. 3) is suited for the containment of a cylindrical bone drill bit 15. Drill bit 15 is on a drill stem 11 for attachment to a drill. The bit 15 having a same outer diameter as the inner diameter of the concave portion 19 of the boat member of the suture transfer device 14. The bit 15 is designed to be used to drill a channel 18 in a bone 16 with the suture transfer device 14 being located upon the drill bit 15 during the drilling process, with the second end 13 of the boat member of suture transfer device 14 following the tip of the drill bit 15 during drilling through the bone 16. Upon completion of the channel 18 through the bone, the suture transfer device 14 remains in the bone, while the drill bit 15 is removed from the bone and the suture transfer device 14 (FIG. 1B). The collar 12 is pulled back to provide access by one or more strands of suture or cable into the boat member into the first end of the boat member without having to pass through the collar 12.

Figure 1A:
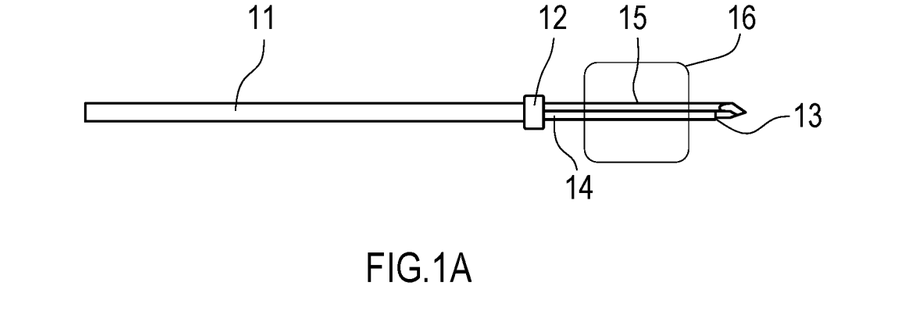
FIGS. 1A-1D are a progressive representation of a method involving the suture transfer device.
Figure 1B:
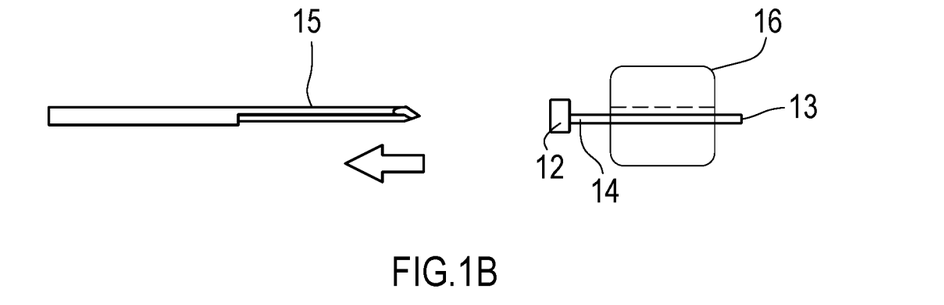
Figure 1C:
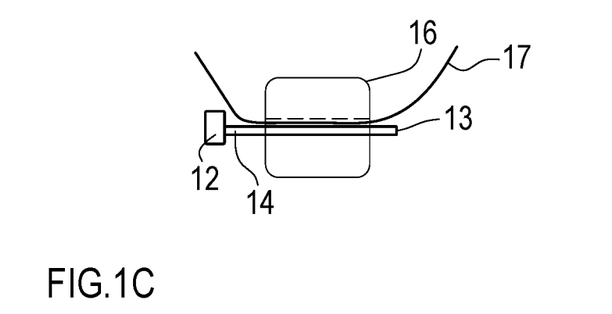
Figure 1D:
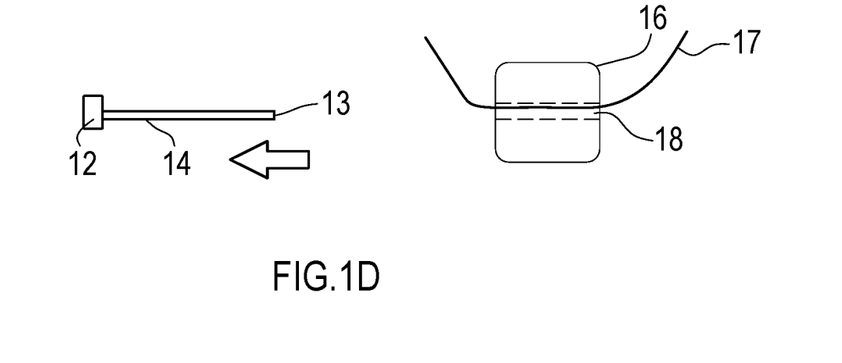
Figure 2:
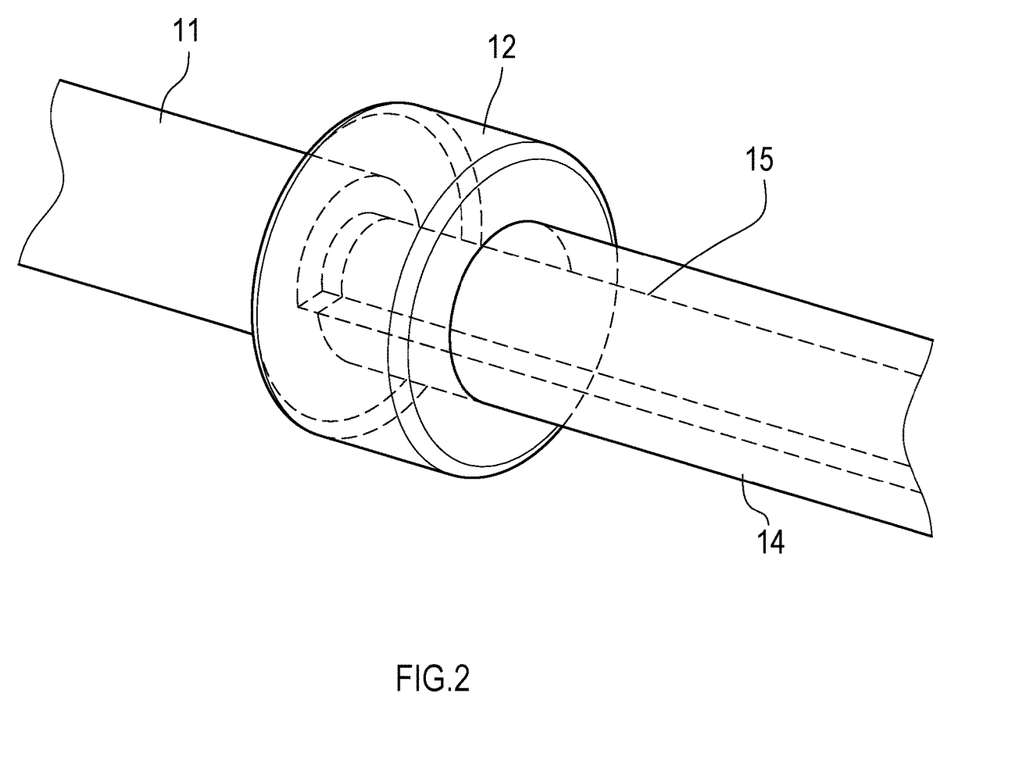
FIG. 2 is a sectional view of the suture transfer device containing the drill bit.

At this time, the suture transfer device 14 extends through the bone 16, with the outer convex portion of the trough portion engaging the drilled channel through the bone, the first end exposed and extending from the entry of the channel 18, the second end 13 extending through the channel 18 with the second end 13 of the boat member extending beyond the channel 18, with the inner concave portion 19 extending completely through the channel 18 providing a smooth surface of the concave trough for passage of one or more sutures or cable completely through the bone during the orthopedic surgical repair as shown in FIG. 1C. Once the repair is complete, the collar 12 is grasped and the suture transfer device 14 is removed from the channel, leaving the installed sutures and cable in place through the bone channel as shown in FIG. 1D.

The suture transfer device may be made of plastic, metal or other biocompatible material, and since it is not contemplated for a permanent installation or application, can be disposable or reusable and does not require concern for long term contact with the bone or soft tissue as would be involved in a device which is intended for permanent of long term existence within the human body. The boat member of the suture transfer device should also be durable to the extent is can withstand the contact of a rotating surgical drill bit without incurring damage to the smooth surface of the inner concave portion of the boat member.

Many methods of use may be contemplated for the suture transfer device. One particular and primary method of using the device, as illustrated in FIGS. 1A-1D, The method is useful for bringing together two bones, two fragments of a single broken bone, attaching another anatomical structure to a bone and similar procedures. For simplicity, FIGS. 1A-1D illustrate the method useful for any such procedure where one drills through a bone to create a channel and at least one suture is passed through the channel at least once. The method contemplates the basic steps as follows:

Step 1—A channel is drilled through a bone 16. (FIG. 1A) This channel is made using a drill 11 composed of two parts, one of which, the drill and bit 15 is going to be removed leaving the second part, the suture transfer device 14 comprising a partial cylinder, in place for passage of the cable/suture 17. (FIG. 1B) When the method is applied to two bones or two bone fragments, once drilling is complete, there are two channels made, one in each bone or bone fragment and each with a suture transfer device 14 comprising a partial cylinder installed.

Step 2—The connection element 17 (cable, suture, etc.) is then passed through the partial cylinder on through the channel to the opposite side. FIG. 1C

Step 3—If two bones or bone fragments are being connected, the connection element 17 is then passed to the far side of the bone connection and threaded through the second partial cylinder of the second suture transfer device placed in a second bone creating a loop.

Step 4—The connection element 17 ends can be connected with a knot or crimp, or additional passes can be made. Various configurations are possible.

Step 5—The connection element 17 is then tightened to the desired tension and tied or crimped thereby creating a secure fixation between the bones in multiple planes with compression.

The method is also useful for connection other anatomical features to a bone. For example, the connection element may be attached to a tendon or ligament before or after passage through the suture transfer device to allow connection of such features to bone.

Figure 6:
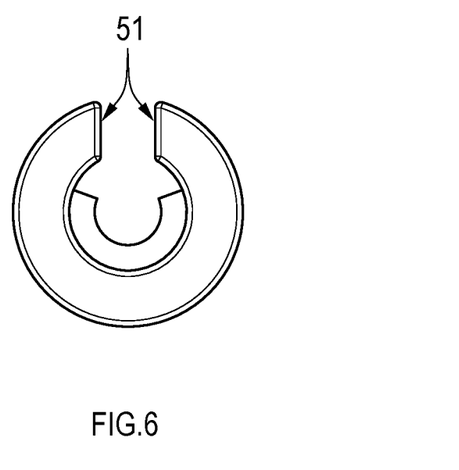
FIG. 6 is an end view of a second embodiment of the collar having an upper aperture for passage of a suture or cable without withdrawal of the suture transfer device.
Figure 7:
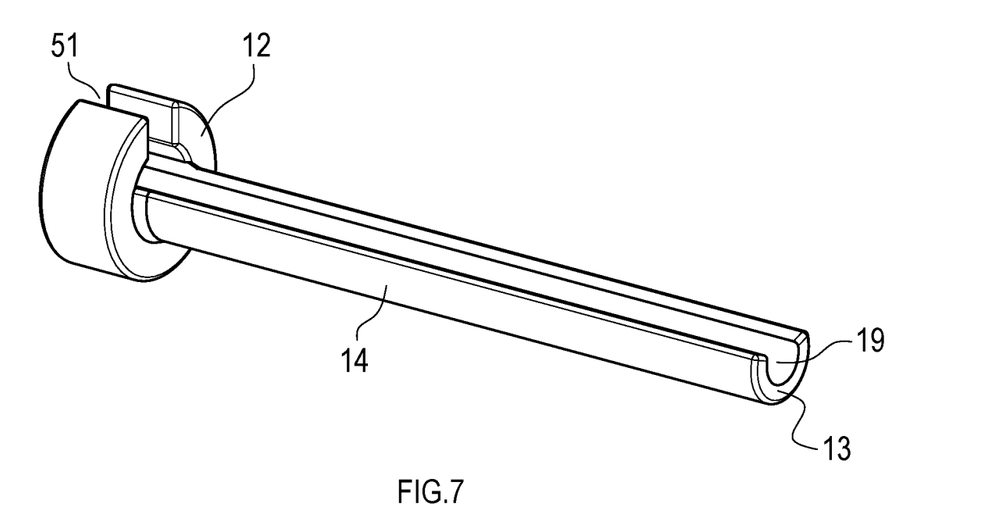
FIG. 7 is a perspective view of a second embodiment including the collar having the upper aperture providing vertical passage of a suture without withdrawal of the suture transfer device.
Figure 8:
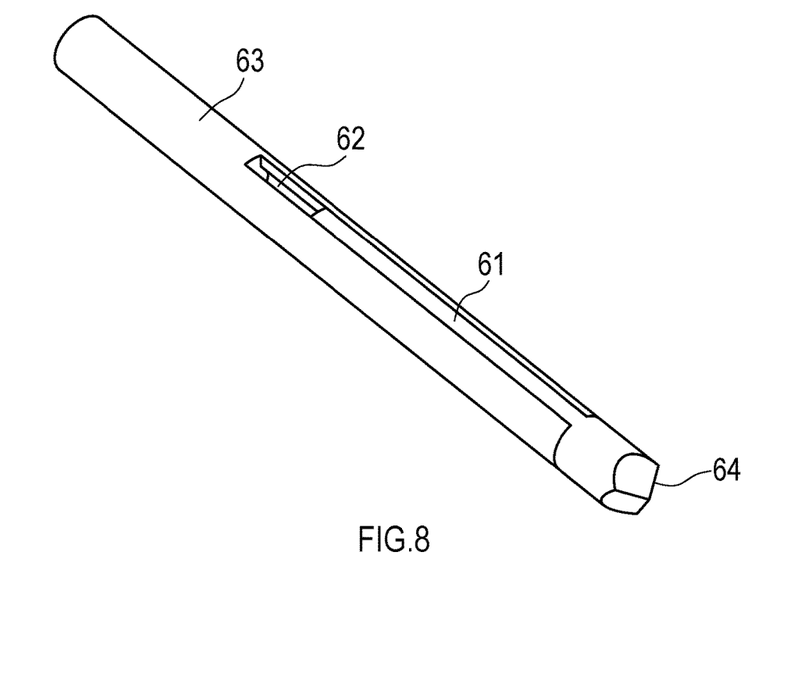
FIG. 8 is a perspective view of a third embodiment of the suture transfer device incorporated into a drill stem of a surgical drill with a removable drill tip installed within the sliding groove channel of the drill stem.

A second embodiment of the suture transfer device, shown in FIGS. 6-7, discloses the suture transfer device with a collar modified from the first embodiment. The collar in the second embodiment has the same or similar central bore with an extended arch portion integrated onto a first end of the suture transfer device, with a second end of the device defining an insertion end. However, in the second embodiment, the extended arch portion further defines an open slot 51 from the central bore to the outer perimeter of the collar. This embodiment does not require the collar to be pulled back, with the sutures and cables freely inserted and installed within the suture transfer device. Removal of the suture transfer device upon completion of the suturing or cabling is still required to complete the use of the second embodiment, as was required in the first embodiment.

Figure 9:
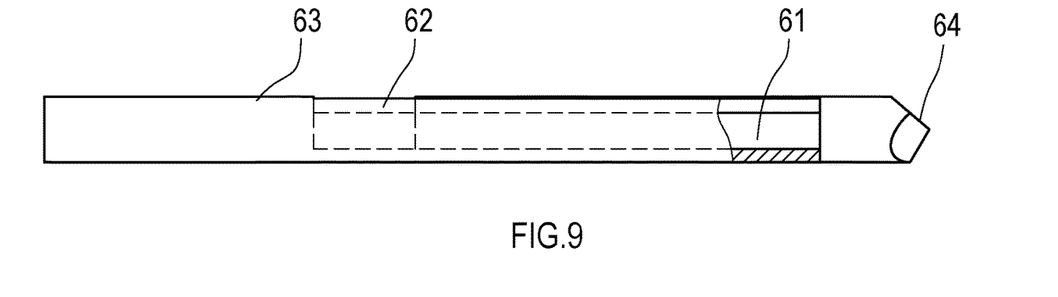
FIG. 9 is a cross sectional side view of FIG. 8.
Figure 10:
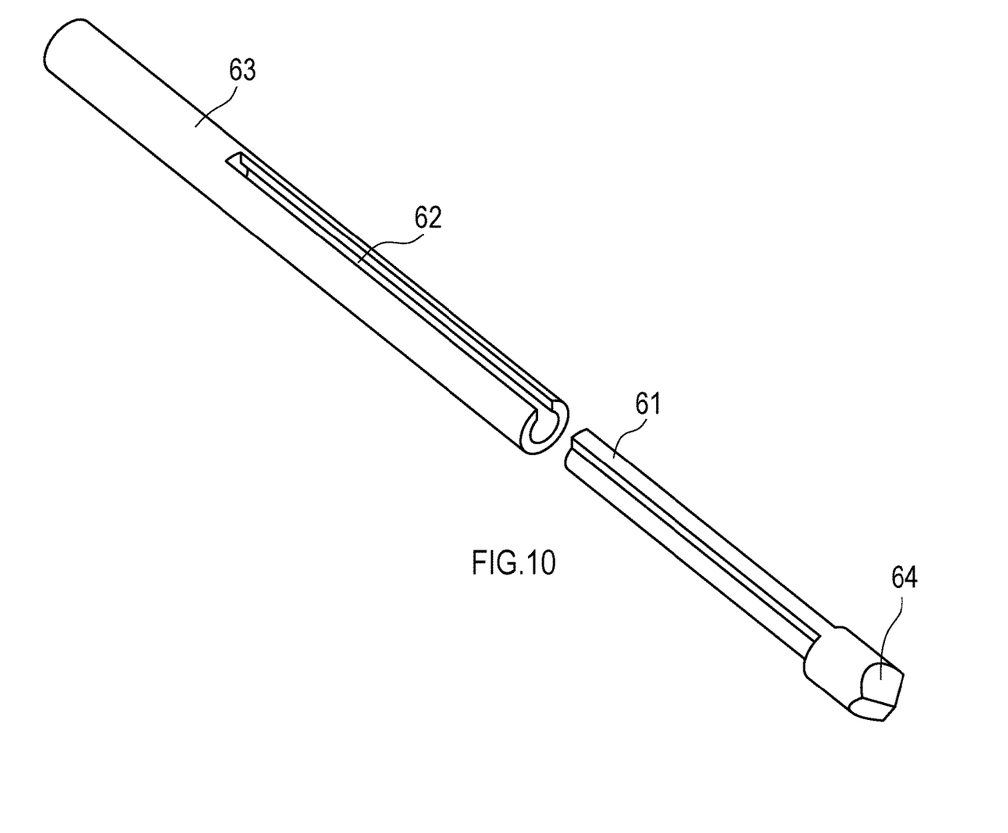
FIG. 10 is a perspective view of a third embodiment of the suture transfer device incorporated into a drill stem of a surgical drill with removable drill tip removed from the drill stem.
Figure 11:
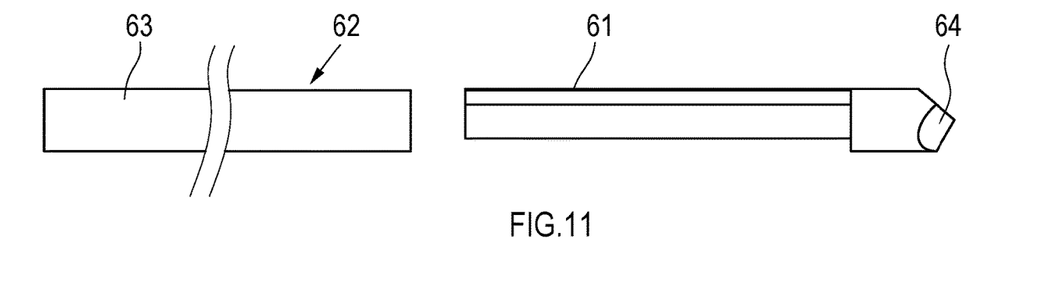
FIG. 11 is a side view of FIG. 10.

A third embodiment of the suture transfer device, shown in FIGS. 8-11, provides for the suture transfer device to be incorporated into the surgical bone drill bit. In this embodiment, the drill bit includes a drill stem 63 defining a drill insertion end and a terminal tool end forming a partial linear slotted channel 62 having a rounded lower margin with an upper linear slot opening the length of the rounded lower margin, the partial linear slot defining an inner origin portion and a terminal end portion extending all the way to the terminal tool end. The partial linear slot is formed away from the drill insertion end so as not to interfere with the attachment of the surgical bone drill bit 61 within a surgical drill tool, as indicated in FIGS. 9 and 11. A drill bit tip 61 defining an outer perimeter forming an insertion end and mating to the diameter, size, configuration, circumference and length of the partial linear slot 62 for sliding insertion within the slot, further defines a bone drilling end with a bone cutting head 64. During the drilling of the bone channel, the drill bit tip 61 is engaged within the linear slot 62. Upon completion of the bone channel, the drill bit tip 61 is removed, exposing the partial linear slot 62 extending through the bone channel. This partial linear slot is positioned to allow passage of one or more sutures or cable through the bone channel within the rounded lower margin just as the first and second embodiments of the suture transfer device accommodated by inclusion of the smooth surface of the concave trough, the rounded lower margin being substantial equivalent of the concave trough. Upon completion of the surgical procedure, the drill stem 63 is withdrawn from the bone channel leaving the sutures and cables deposited and secured within the bone channel.

The design of the mated suture transfer device and drill bit shown in FIGS. 8-11 is not limiting on the devices provided by this invention. The design of the mated surfaces may be concave on the suture transfer device and convex on the drill bit head and they may also have other configurations. As described herein for the suture transfer device, the surface of the inner portion of the device can be made with a variety of configuration including multi-angular and combined concave and multi-angular. For each configuration chosen for the inner surface of the suture transfer device, a drill bit head with a matching exterior surface can be provided.

In a fourth embodiment, a kit is provided comprising a selected number of suture transfer devices. The devices can be chosen for any particular kit based on factors such as the size of the bones to be addressed in surgery, the length of the channels to be bored and other factors. Kits can provide suture transfer devices for a narrow or a large range of applications. A kit can include suture transfer devices and matched drill bits in the same kit. Kit can also provide connection elements along with suture transfer devices wherein the degrees of circumference of the outer surface of the semi-cylindrical portion of the device is chosen as appropriate for use with the connection elements provided in the kit.

A kit for passing sutures through a channel in bone can comprise at least one suture transfer device in at least one length and at least one diameter. The kit can further comprise at least one drill bit matched for use with said at least one suture transfer device. The kit can further comprise at least one connection element.

The following describe aspects of the invention:

1. A suture transfer device for passing a connection element through a channel drilled through a bone, comprising a semi-cylindrical portion having a first end and a second end, an inner surface and an exterior convex surface, and said inner surface being sized to define a trough within the semi-cylindrical portion, and said exterior convex surface sized to be smaller than the diameter of the channel drilled through a bone, and said device having an overall length greater than the length of the channel drilled through a bone, and said inner surface providing a passageway for a connection element when the device is within the channel drilled through a bone.

2. The device of paragraph 1 further comprising an extension protruding from the first or second end of the device.

3. The device of paragraph 2 wherein the extension protrudes at an angle from zero degrees to ninety degrees from the longitudinal axis of the device.

4. The device of paragraph 2 wherein the extension comprises a collar.

5. A suture transfer device adapted for use with a drill bit having a drill stem and a bone cutting head comprising a semi-cylindrical portion having a first end and a second end, an inner concave surface and an exterior convex surface, and said inner concave surface being sized to accept a drill bit seated within the semi-cylindrical portion, and said exterior convex surface sized to match the bore produced by the bone cutting head of the drill bit, and said first end adapted to collinearly align with the drill stem of the drill bit, and said second end adapted to seat against the bone cutting head of the drill bit.

6. The suture transfer device of paragraph 5 further comprising a collar on the first end of the device, said collar having a central opening with a first portion and a second portion, said first portion being adapted to accept the drill bit through the opening, and said second portion being contiguously aligned with the inner convex surface of the semi-cylindrical portion of the device, wherein the stem of the drill bit seats against the collar.

7. The suture transfer device of paragraph 5 further comprising a collar on the first end of the device, said collar having a central opening with a first portion and a second portion, said first portion being adapted to accept the drill bit through the opening, and said second portion being larger than the diameter of the semi-circular portion of the device, said second portion adapted to accept the drill stem of the drill bit and provides for the stem to seat against the first end of the semi-cylindrical portion of the device.

8. The suture transfer device of paragraph 5 wherein the device is comprised of metal.

9. The suture transfer device of paragraph 5 wherein the device is comprised of plastic.

10. The suture transfer device of paragraph 5 wherein the first end of the suture transfer device is collinearly fused to the stem of the drill bit and the semi-cylindrical portion is adapted to accept a drill bit bone cutting head within the semi-cylindrical portion.

11. A method of passing a suture through a channel in a bone comprising; providing a suture transfer device adapted for use with a drill bit having a drill stem and a bone cutting head comprising, a semi-cylindrical portion having a first end and a second end, an inner concave surface and an exterior convex surface, said inner concave surface being sized to accept a drill bit seated within the semi-cylindrical portion, said exterior convex surface sized to match the bore produced by the bone cutting head of the drill bit, said first end adapted to align with the drill stem of the drill bit, and said second end adapted to seat against the bone cutting head of the drill bit, and combining the suture transfer device with the drill bit, and drilling a first channel through a bone with the combined drill bit and suture transfer device, and withdrawing the drill bit from the suture transfer device leaving the suture transfer device in the channel, and passing a connection element through the first channel through the bone, and removing the suture transfer device from the first channel.

12. The method of paragraph 11 wherein the first end of the suture transfer device is collinearly fused to the stem of the drill bit and the semi-cylindrical portion is adapted to accept a drill bit bone cutting head within the semi-cylindrical portion.

13. The method of paragraph 11 wherein a second suture transfer device is combined with a drill bit, a second channel is drilled in a second bone, the drill bit is withdrawn from the second channel and said connection element is passed through both the first and second channels.

14. The method of paragraph 11 wherein the connection element is attached to an anatomical feature that is a tendon or ligament before or after it is passed through the first channel.

15. The method of paragraph 11 wherein the connection element is passed through the first channel more than once.

16. The method of paragraph 15 wherein the connection element is passed through the first channel and the second channel more than once.

Other contemplated methods of use for the suture transfer device may be present, with the utility of the device being suited for other applied uses in the orthopedic surgical arts as well as other surgical arts, medical applications and medical uses. Although the embodiments of the invention have been described and shown above, it will be appreciated by those skilled in the art that numerous modifications may be made therein without departing from the scope of the invention as herein described.

What is claimed:

1. A suture transfer device for passing a connection element through a channel drilled through a bone, comprising:
   a drill bit, said drill bit having a drill stem and a bone cutting head that produces a bore in bone, and
   a suture transfer device having a semi-cylindrical portion having a first end and a second end, an inner surface and an exterior convex surface, and said inner surface being sized to define a trough within the semi-cylindrical portion, and said inner surface being sized to accept said drill bit seated within the semi-cylindrical portion said exterior convex surface sized to match the bore produced by the bone cutting head of the drill bit, and said suture transfer device having an overall length greater than the length of the channel drilled through a bone, and said inner surface providing a passageway for a connection element when the device is within the channel drilled through a bone, and a collar on said first end of the device, said collar having a central bore, and said collar further defines an open slot from the central bore to the outer perimeter of the collar, and said second end of the device defining an insertion end, and said second end adapted to seat against the bone cutting head of the drill bit, and a suture, said suture being sized to be able to be passed through the suture transfer device at least twice.

2. The device of claim 1 wherein the collar protrudes at an angle from zero degrees to ninety degrees from the longitudinal axis of the device.

3. The suture transfer device of claim 1 further comprising; said collar having a central opening with a first portion and a second portion, said first portion being adapted to accept the drill bit through the opening, and said second portion being contiguously aligned with the trough of the semi-cylindrical portion of the device, wherein the stem of the drill bit seats against the collar.

4. The suture transfer device of claim 1 further comprising; said collar having a central opening with a first portion and a second portion, said first portion being adapted to accept the drill bit through the opening, and said second portion being larger than the diameter of the semi-cylindrical portion of the device, said second portion adapted to accept the drill stem of the drill bit and provides for the stem to seat against the first end of the semi-cylindrical portion of the device.

5. The suture transfer device of claim 1 wherein the device is comprised of metal.

6. The suture transfer device of claim 1 wherein the device is comprised of plastic.

* * * * *